US012123062B2

(12) United States Patent
Singh et al.

(10) Patent No.: US 12,123,062 B2
(45) Date of Patent: Oct. 22, 2024

(54) **METHODS AND COMPOSITIONS FOR DETERMINING *SALMONELLA* PRESENCE AND CONCENTRATION USING PCR PRIMERS OF VARYING AMPLIFICATION EFFICIENCIES**

(71) Applicants: The Florida State University Research Foundation, Inc., Tallahassee, FL (US); The United State of America, as presented by the Secretary of Agriculture, Washington, DC (US)

(72) Inventors: Prashant Singh, Tallahassee, FL (US); Joseph M. Bosilevac, Clay Center, NE (US)

(73) Assignees: The Florida State University Research Foundation, Inc., Tallahassee, FL (US); The United States of America, as presented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 18/054,778

(22) Filed: Nov. 11, 2022

(65) Prior Publication Data
US 2023/0265529 A1    Aug. 24, 2023

Related U.S. Application Data

(60) Provisional application No. 63/278,566, filed on Nov. 12, 2021.

(51) Int. Cl.
C12Q 1/68 (2018.01)
C12Q 1/689 (2018.01)
C12R 1/42 (2006.01)

(52) U.S. Cl.
CPC ......... *C12Q 1/689* (2013.01); *C12Q 2600/16* (2013.01); *C12R 2001/42* (2021.05)

(58) Field of Classification Search
CPC .................. C12R 2001/42; C12Q 2600/16
See application file for complete search history.

(56) References Cited

U.S. PATENT DOCUMENTS

| 10,501,814 B2 | 12/2019 | Hogan et al. | |
| 2003/0050470 A1 * | 3/2003 | An ......................... | C07H 21/00 435/6.14 |
| 2021/0292816 A1 | 9/2021 | Singh | |
| 2023/0265529 A1 * | 8/2023 | Singh ..................... | C12Q 1/689 435/6.12 |

FOREIGN PATENT DOCUMENTS

| WO | 2012/145557 | 10/2012 | |
| WO | 2017/007852 | 1/2017 | |
| WO | 2017/067942 | 4/2017 | |
| WO | 2017/194732 | 11/2017 | |
| WO | 2021/072057 | 4/2021 | |
| WO | 2021/102313 | 5/2021 | |
| WO | WO-2023086942 A2 * | 5/2023 | ............. C12Q 1/689 |

OTHER PUBLICATIONS

Enany et al., 2018. Comparison between different methods for detection of Salmonella species in imported and local duckling. Suez Canal Veterinary Medical Journal. SCVMJ, 23(1), pp. 171-180. (Year: 2018).*
Gadberry MD, Malcomber ST, Doust AN, Kellogg EA. Primaclade—a flexible tool to find conserved PCR primers across multiple species. Bioinformatics. Apr. 1, 2005; 21(7):1263-4. Epub Nov. 11, 2004. (Year: 2005).*
Genbank Accession No. L16014—*Salmonella typhimurium enterotoxin* (stn) gene, complete cds (submitted Sep. 7, 1994, retrieved on Sep. 28, 2023 from http://www.ncbi.nlm.nih.gov/nuccore/L16014). (Year: 1994).*
Genbank Accession No. ON032650—*Salmonella enterica* subsp. enterica serovar Typhimurium strain GH_9 Stn (stn) gene, partial cds (submitted Mar. 19, 2022, retrieved on Sep. 28, 2023 from http://www.ncbi.nlm.nih.gov/nuccore/ON032650).*
Kim, S.H., Lee, Y.S., Joo, I.S., Kwak, H.S., Chung, G.T. and Kim, S.H., 2018. Rapid detection for *Salmonella* spp. by ultrafast real-time PCR assay. J. Food Hyg. Saf, 33, pp. 50-57. (Year: 2018).*
Lan et al., 2018. Distribution of virulence genes among *Salmonella* serotypes isolated from pigs in Southern Vietnam. Journal of food protection, 81(9), pp. 1459-1466. (Year: 2018).*
Liu et al., 2018. Multiplex high resolution melt-curve real-time PCR assay for reliable detection of *Salmonella*. Food Control, 91, pp. 225-230. (Year: 2018).*
Malorny, B., 2013. Diagnostic real-time PCR for detection of *Salmonella* in food and characterization of epidemiologically important *Salmonella enterica* subsp. enterica serovars isolated from livestock, food and humans. Thesis. (Year: 2013).*
Moore et al., 2007. Real-time PCR method for *Salmonella* spp. targeting the stn gene. Journal of applied microbiology, 102(2), pp. 516-530. (Year: 2007).*
Saini et al., 2019. Multiplexed Stn and PlcA based specific genetic marker for early detection of *Salmonella enterica* and Listeria monocytogenes in milk samples. The Annals of the University Dunarea de Jos of Galati. Fascicle VI—Food Technology, 43(2), pp. 9-20. (Year: 2019).*

(Continued)

*Primary Examiner* — Stephanie K Mummert
*Assistant Examiner* — Olayinka A Oyeyemi
(74) *Attorney, Agent, or Firm* — Meunier Carlin & Curfman LLC (57) ABSTRACT

Disclosed herein are methods and kits for quantifying the presence of a microorganism in a sample. Specifically, disclosed are methods for quantifying a pathogen in a sample, such as a food sample, to determine if the levels of pathogen present in the sample are within an acceptable range.

4 Claims, 2 Drawing Sheets

Specification includes a Sequence Listing.

(56) References Cited

OTHER PUBLICATIONS

SantaLucia Jr, John. Physical principles and visual-OMP software for optimal PCR design. PCR Primer Design. Humana Press, 2007: pp. 3-33. (Year: 2007).*

Vichaibun et al., 2020. Quantitative LAMP and PCR detection of *Salmonella* in chicken samples collected from local markets around Pathum Thani province, Thailand. International journal of food science, 2020, pp. 1-6. (Year: 2020).*

Genbank Accession No. LC227778—*Salmonella enterica* stn gene for enterotoxin, partial cds, strain: AHG-6, submitted Mar. 2017, retrieved on Jan. 12, 2024 from http://www.ncbi.nlm.nih.gov/nuccore/LC227778). (Year: 2017).*

Hussong, D.; Enkiri, N.K.; Burge, W.D. Modified Agar Medium for Detecting Environmental *Salmonellae* by the Most-Probable-Number Method. Appl. Environ. Microbiol. 1984, 48, 1026-1030.

Liu, Y.; Singh, P.; Mustapha, A. Multiplex High Resolution Melt-Curve Real-Time PCR Assay for Reliable Detection of *Salmonella*. Food Control 2018, 91, 225-230, doi:10.1016/j.foodcont.2018.03.043.

Anderson, A.; Pietsch, K.; Zucker, R.; Mayr, A.; Müller-Hohe, E.; Messelhäusser, U.; Sing, A.; Busch, U.; Huber, I. Validation of a Duplex Real-Time PCR for the Detection of *Salmonella* Spp. in Different Food Products. Food Anal. Methods 2011, 4, 259-267, doi: 10.1007/s12161-010-9142-8.

Blaser, M.J.; Newman, L.S. A Review of Human Salmonellosis: I. Infective Dose. Rev Infect Dis 1982, 4, 1096-1106, doi: 10.1093/clinids/4.6.1096.

Lee, K.-M.; Runyon, M.; Herrman, T.J.; Phillips, R.; Hsieh, J. Review of *Salmonella* Detection and Identification Methods: Aspects of Rapid Emergency Response and Food Safety. Food Control 2015, 47, 264-276, doi:10.1016/j.foodcont.2014.07.011.

Ponder, M.A. The Effects of Food Composition on Foodborne Illness Infectious Dose and Host Susceptibility. In Foodborne Pathogens: Virulence Factors and Host Susceptibility; Gurtler, J.B., Doyle, M.P., Kornacki, J.L., Eds.; Food Microbiology and Food Safety; Springer International Publishing: Cham, 2017; pp. 469-494 ISBN 978-3-319-56836-2.

Santos, F.B.O.; Li, X.; Payne, J.B.; Sheldon, B.W. Estimation of Most Probable Number *Salmonella* Populations on Commercial North Carolina Turkey Farms. Journal of Applied Poultry Research 2005, 14, 700-708, doi: 10.1093/japr/14.4.700.

Singh, P.; Liu, Y.; Bosilevac, J.M.; Mustapha, A. Detection of Shiga Toxin-Producing *Escherichia coli*, stx1, stx2 and *Salmonella* by Two High Resolution Melt Curve Multiplex Real-Time PCR. Food Control 2019, 96, 251-259, doi: 10.1016/j.foodcont.2018.09.024.

Singh, P.; Mustapha, A. Multiplex TaqMan® Detection of Pathogenic and Multi-Drug Resistant *Salmonella*. Int. J. Food Microbiol. 2013, 166, 213-218, doi: 10.1016/j.ijfoodmicro.2013.07.023.

USDA, FSIS Primer and Probe Sequences and Reagent Concentrations for Non-O157 Shiga Toxin-Producing *Escherichia coli* (STEC) Real-Time PCR Assay. MLG 5C Appendix 4.00 2019.

International Search Report and Written Opinion issued for Application No. PCT/US2022/079721, dated Apr. 18, 2023.

* cited by examiner

SEQUENCE LISTING

```
Sequence total quantity: 19
SEQ ID NO: 1            moltype = DNA   length = 21
FEATURE                 Location/Qualifiers
source                  1..21
                        mol_type = other DNA
                        organism = Salmonella typhurium
SEQUENCE: 1
gccatgctgt tcgatgatat a                                              21

SEQ ID NO: 2            moltype = DNA   length = 20
FEATURE                 Location/Qualifiers
source                  1..20
                        mol_type = other DNA
```

```
                              organism = Salmonella typhurium
SEQUENCE: 2
ggatcagttg gaggcgattt                                                       20

SEQ ID NO: 3              moltype = DNA  length = 20
FEATURE                   Location/Qualifiers
source                    1..20
                          mol_type = other DNA
                          organism = Salmonella typhurium
SEQUENCE: 3
gtcccgtcag ctttggtcgt                                                       20

SEQ ID NO: 4              moltype = DNA  length = 20
FEATURE                   Location/Qualifiers
source                    1..20
                          mol_type = other DNA
                          organism = Salmonella typhurium
SEQUENCE: 4
cggtgggttt tgttgtcttc                                                       20

SEQ ID NO: 5              moltype = DNA  length = 19
FEATURE                   Location/Qualifiers
source                    1..19
                          mol_type = other DNA
                          organism = Salmonella typhurium
SEQUENCE: 5
tcatcgcacc gtcaaagga                                                        19

SEQ ID NO: 6              moltype = DNA  length = 25
FEATURE                   Location/Qualifiers
source                    1..25
                          mol_type = other DNA
                          organism = Salmonella typhurium
SEQUENCE: 6
ctctggatgg tatgcccggt aaaca                                                 25

SEQ ID NO: 7              moltype = DNA  length = 19
FEATURE                   Location/Qualifiers
source                    1..19
                          mol_type = other DNA
                          organism = Salmonella typhurium
SEQUENCE: 7
gcaggtgcct ttctccatt                                                        19

SEQ ID NO: 8              moltype = DNA  length = 19
FEATURE                   Location/Qualifiers
source                    1..19
                          mol_type = other DNA
                          organism = Salmonella typhurium
SEQUENCE: 8
gcaggtgcct ttatccatt                                                        19

SEQ ID NO: 9              moltype = DNA  length = 20
FEATURE                   Location/Qualifiers
source                    1..20
                          mol_type = other DNA
                          organism = Salmonella typhurium
SEQUENCE: 9
agcgtattgg tgccttcaac                                                       20

SEQ ID NO: 10             moltype = DNA  length = 18
FEATURE                   Location/Qualifiers
source                    1..18
                          mol_type = other DNA
                          organism = Salmonella typhurium
SEQUENCE: 10
ctggctgtct cctctgcg                                                         18

SEQ ID NO: 11             moltype = DNA  length = 19
FEATURE                   Location/Qualifiers
source                    1..19
                          mol_type = other DNA
                          organism = Salmonella typhurium
SEQUENCE: 11
cctcttgcca tcggatgtg                                                        19

SEQ ID NO: 12             moltype = DNA  length = 21
FEATURE                   Location/Qualifiers
source                    1..21
```

```
                            mol_type = other DNA
                            organism = Salmonella typhurium
SEQUENCE: 12
ggctggtcat cctctcagac c                                                      21

SEQ ID NO: 13               moltype = DNA  length = 26
FEATURE                     Location/Qualifiers
source                      1..26
                            mol_type = other DNA
                            organism = Salmonella typhurium
SEQUENCE: 13
gtggggtaac ggctcaccta ggcgac                                                 26

SEQ ID NO: 14               moltype = DNA  length = 24
FEATURE                     Location/Qualifiers
source                      1..24
                            mol_type = other DNA
                            organism = Salmonella typhurium
SEQUENCE: 14
ccagtttatc gttattacca aagg                                                   24

SEQ ID NO: 15               moltype = DNA  length = 19
FEATURE                     Location/Qualifiers
source                      1..19
                            mol_type = other DNA
                            organism = Salmonella typhurium
variation                   18
                            note = N CAN BE ANY NUCLEOTIDE
SEQUENCE: 15
atcgcaccgt caaagganc                                                         19

SEQ ID NO: 16               moltype = DNA  length = 20
FEATURE                     Location/Qualifiers
source                      1..20
                            mol_type = other DNA
                            organism = Salmonella typhurium
SEQUENCE: 16
sgatcakytg gaggcgattt                                                        20

SEQ ID NO: 17               moltype = DNA  length = 24
FEATURE                     Location/Qualifiers
source                      1..24
                            mol_type = other DNA
                            organism = Salmonella typhurium
SEQUENCE: 17
gatgttyctt agcgcyttac aggc                                                   24

SEQ ID NO: 18               moltype = DNA  length = 24
FEATURE                     Location/Qualifiers
source                      1..24
                            mol_type = other DNA
                            organism = Salmonella typhurium
SEQUENCE: 18
ccgacmgcgt aatatttggc tgac                                                   24

SEQ ID NO: 19               moltype = DNA  length = 23
FEATURE                     Location/Qualifiers
source                      1..23
                            mol_type = other DNA
                            organism = Salmonella typhurium
SEQUENCE: 19
cgtcrgtgga ttwccgtcgc cct                                                    23
```

METHODS AND COMPOSITIONS FOR DETERMINING *SALMONELLA* PRESENCE AND CONCENTRATION USING PCR PRIMERS OF VARYING AMPLIFICATION EFFICIENCIES

CROSS-REFERENCE TO RELATED APPLICATIONS

This application claims benefit of U.S. Provisional Application No. 63/278,566, filed Nov. 12, 2021, incorporated herein by reference in its entirety.

SEQUENCE LISTING

This application incorporates by reference the Sequence listing in the file, "10850-056US1 2022_11_11 Sequence Listing.xml", file size 17.7 KB, created Nov. 10, 2022.

BACKGROUND

Knowing a target organism's concentration range in the biological sample is critical for many industries, including the food and diagnostic industries. For example, foodborne pathogens (i.e., *Salmonella, Campylobacter*), which are not considered an adulterant in food, can be present in food samples at varying concentrations. A food sample with 0.1 $\log_{10}$ CFU/g of these pathogens presents a lower hazard compared to a sample with 5 $\log_{10}$ CFU/g.

Current methods of estimating the concentrations of microorganisms are based on the most probable number (MPN) methods. The MPN method is a slow, culture-based, laborious method that requires two or more days for completion. For instance, beef or poultry processors who wish to act on *Salmonella* concentrations greater than 1 or 10 CFU/g of meat currently have to rely on MPN based method. Some current molecular methods on the market can provide this concentration determination, but they rely on an external standard curve, and regression are required to measure organism concentration. As each sample varies in composition, microbial load, and presence of natural inhibitor (i.e., sample matrix effect for each sample type), a separate standard curve is needed.

PCR is a rapid molecular method that can identify specific microorganisms either directly in a sample or after a short incubation period of 4-16 hours. Some pathogen detection assays rely on the enrichment of samples for increasing the number of target pathogens in the biological sample (i.e., food, meat, blood, urine, tissue, swabs). DNA isolated from these enrichments is used for the amplification of specific DNA sequences in a PCR reaction. These commercially available PCR assays generate only the presence or absence of results, and are not geared to detect varying levels of the pathogen in the test samples. What is needed in the art are methods and compositions for detecting not only the presence of an organism, but the estimated number of organisms present in the test sample.

SUMMARY

Disclosed herein are sets of primers comprising 80% or more identity to SEQ ID NOS: 1 and 2; 4 and 5; 14 and 15; 7 and/or 8 and 9; and 11 and 12.

Also disclosed is a nucleic acid probe for amplifying an amplification product produced by the primers of claim 1, wherein said probe comprises 80% or more identity to SEQ ID NO: 3, 6, 10, 13, or 19.

Disclosed herein is a method for quantifying an amount of target nucleic acid from *Salmonella* in a sample, the method comprising: a) providing a sample comprising at least one target nucleic acid; b) dividing the sample of step a) into at least two containers; c) amplifying the target nucleic acid in each container by exposing each sample to a different set of primers in uniplex or multiplex under conditions suitable for nucleic acid amplification, wherein said primers comprise at least one forward primer with 80% or more identity to SEQ ID NO: 1, 4, 7, 8, 11, 14, or 17, and at least one reverse primer with 80% or more identity to SEQ ID NO: 2, 5, 9, 12, 15, 16, or 18, and further wherein at least one primer in each primer set has varying specificity for the target nucleic acid compared to the others, thereby creating an amplification product; d) exposing the amplification product to a probe which is 100% specific for the target nucleic acid, wherein said probe is 100% identical to at least one of SEQ ID NOS: 3, 6, 10, 13, or 19; and e) determining which of the containers showed a detectable level of amplification using the probe, thereby quantifying the amount of target nucleic acid in the sample.

Further disclosed are kits for quantification of a target nucleic acid in a sample, wherein the kit comprises: at least two containers, wherein each container comprises appropriate reagents for nucleic acid amplification, including a set of primers, wherein each primer set comprises a forward and reverse primer, and further wherein each primer set in each container differs from at least one other primer set in one other container by 1, 2, 3, 4, or 5 nucleotides; a probe specific for the target nucleic acid, wherein said probe is 100% identical to at least one of SEQ ID NOS: 3, 6, 10, 13, or 19.

BRIEF DESCRIPTION OF THE FIGURES

The accompanying drawings, which are incorporated in and constitute a part of this specification, illustrate certain examples of the present disclosure and, together with the description, serve to explain, without limitation, the principles of the disclosure. Like numbers represent the same elements throughout the figures.

DETAILED DESCRIPTION

Figure 1A:
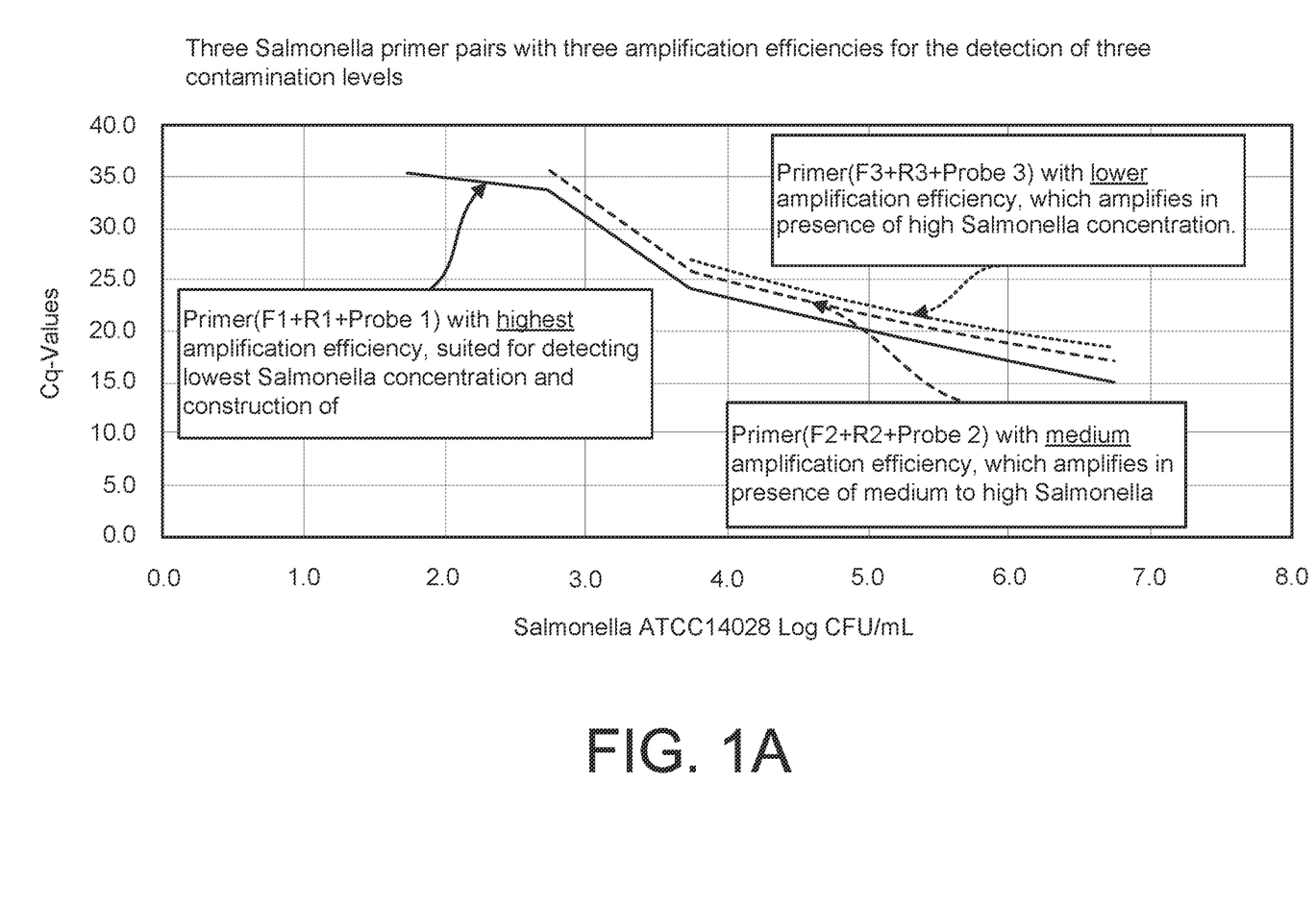
FIGS. 1A and 1B show different views of a standard curve for three selected primer pairs.
Figure 1B:
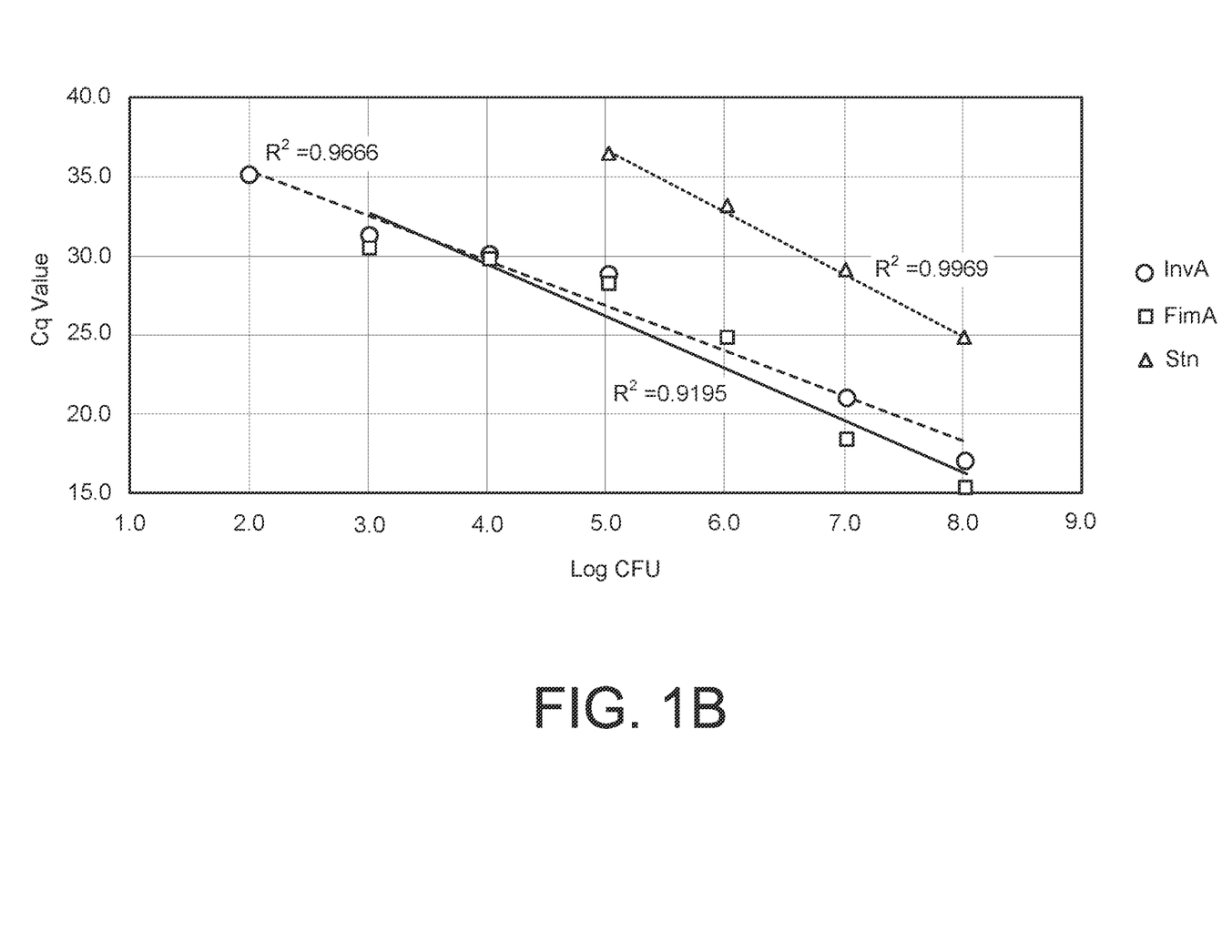

The following description of the disclosure is provided as an enabling teaching of the disclosure in its best, currently known embodiment. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Definitions

In this specification and in the claims which follow, reference will be made to a number of terms which shall be defined to have the following meanings:

As used herein, the singular forms "a," "an" and "the" include plural referents unless the context clearly dictates otherwise. Thus, for example, reference to a "metal" includes examples having two or more such "metals" unless the context clearly indicates otherwise.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, "complementary" or "complementarity" refers to the ability of a nucleotide in a polynucleotide molecule to form a base pair with another nucleotide in a second polynucleotide molecule. For example, the sequence 5'-A-C-T-3' is complementary to the sequence 3'-T-G-A-5'. Complementarity may be partial, in which only some of the nucleotides match according to base pairing, or complete, where all the nucleotides match according to base pairing. For purposes of the present invention, "substantially complementary" refers to 90% or greater identity over the length of the target base pair region. The complementarity can also be 50, 60, 70, 75, 80, 85, 90, 91, 92, 93, 94, 95, 96, 97, 98, 99, or 100% complementary, or any amount below or in between these amounts.

As used herein, "nucleic acid sequence" refers to the order or sequence of nucleotides along a strand of nucleic acids. In some cases, the order of these nucleotides may determine the order of the amino acids along a corresponding polypeptide chain. The nucleic acid sequence thus codes for the amino acid sequence. The nucleic acid sequence may be single-stranded or double-stranded, as specified, or contain portions of both double-stranded and single-stranded sequences. The nucleic acid sequence may be composed of DNA, both genomic and cDNA, RNA, or a hybrid, where the sequence comprises any combination of deoxyribo- and ribo-nucleotides, and any combination of bases, including uracil (U), adenine (A), thymine (T), cytosine (C), guanine (G), inosine, xathanine hypoxathanine, isocytosine, isoguanine, etc. It may include modified bases, including locked nucleic acids, peptide nucleic acids and others known to those skilled in the art.

An "oligonucleotide" is a polymer comprising two or more nucleotides. The polymer can additionally comprise non-nucleotide elements such as labels, quenchers, blocking groups, or the like. The nucleotides of the oligonucleotide can be natural or non-natural and can be unsubstituted, unmodified, substituted or modified. The nucleotides can be linked by phosphodiester bonds, or by phosphorothioate linkages, methylphosphonate linkages, boranophosphate linkages, or the like.

A "primer" is a nucleic acid that contains a sequence complementary to a region of a template nucleic acid strand and that primes the synthesis of a strand complementary to the template (or a portion thereof). Primers are typically 18-20 base long, but need not be, relatively short, chemically synthesized oligonucleotides (typically, deoxyribonucleotides). In an amplification, e.g., a PCR amplification, a pair of primers typically define the 5' ends of the two complementary strands of the nucleic acid target that is amplified.

By "capture sequence," which is also referred to herein as a "second nucleic acid sequence" is meant a sequence which hybridizes to the target nucleic acid and allows the first nucleic acid sequence, or primer sequence, to be in close proximity to the target region of the target nucleic acid.

A "target region" is a region of a target nucleic acid that is to be amplified, detected or both.

The "Tm" (melting temperature) of a nucleic acid duplex under specified conditions is the temperature at which half of the nucleic acid sequences are disassociated and half are associated. As used herein, "isolated Tm" refers to the individual melting temperature of either the first or second nucleic acid sequence in the cooperative nucleic acid when not in the cooperative pair. "Effective Tm" refers to the resulting melting temperature of either the first or second nucleic acid when linked together.

As used herein, "amplify, amplifying, amplifies, amplified, amplification" refers to the creation of one or more identical or complementary copies of the target DNA. The copies may be single stranded or double stranded. Amplification can be part of a number of processes such as the extension of a primer, reverse transcription, polymerase chain reaction, nucleic acid sequencing, rolling circle amplification and the like.

As used herein, "purified" refers to a polynucleotide, for example a target nucleic acid sequence, that has been separated from cellular debris, for example, high molecular weight DNA, RNA and protein. This would include an isolated RNA sample that would be separated from cellular debris, including DNA. It can also mean non-native, or non-naturally occurring nucleic acid.

As used herein, "protein," "peptide," and "polypeptide" are used interchangeably to denote an amino acid polymer or a set of two or more interacting or bound amino acid polymers.

As used herein, "stringency" refers to the conditions, i.e., temperature, ionic strength, solvents, and the like, under which hybridization between polynucleotides occurs. Hybridization is the process that occurs between the primer and template DNA during the annealing step of the amplification process.

As used herein, "multiplex" refers to the use of PCR to amplify several different DNA targets (genes) simultaneously in a single assay or reaction. Multiplexing can amplify nucleic acid samples, such as genomic DNA, cDNA, RNA, etc., using multiple primers and any necessary reagents or components in a thermal cycler.

As used herein, "enrichment" refers to conditions favoring the growth of a particular microorganism. For example, in one embodiment, a method of the present invention may benefit from an enrichment step whereby bacterial cells or a solution obtained by homogenizing a biological sample and containing one or more target bacterial cells or species are placed in an enrichment medium to allow for the growth of the target bacterial species or strains for the purposes of detection of the bacterial cells or species.

As used herein, a "sample" is from any source, including, but not limited to, a gas sample, a fluid sample, a solid sample, or any mixture thereof. The sample can be from any source, including food, water, plants or animals, solid or liquid waste, etc.

As used herein, a "microorganism" or "organism" includes, but is not limited to, a virus, viroids, bacteria, archaea, fungi, protozoa, and the like.

The term "sensitivity" refers to a measure of the proportion of actual positives which are correctly identified as such.

The term "confidence level" refers to the likelihood, expressed as a percentage, that the results of a test are real and repeatable and not random. Confidence levels are used to indicate the reliability of an estimate and can be calculated by a variety of methods.

As used herein, the term "subject," "patient," or "organism" includes humans and mammals (e.g., mice, rats, pigs, cats, dogs, and horses). Typical subjects for which methods of the present invention may be applied will be mammals, such as humans. A wide variety of subjects will be suitable for veterinary, diagnostic, research, or food safety applications, e.g., humans; livestock such as cattle, sheep, goats, cows, swine, and the like; poultry such as chickens, ducks, geese, turkeys, and the like; and domesticated animals, particularly pets such as dogs and cats. The term "living subject" refers to a subject as noted above or another organism that is alive.

As used herein, the term "culture media" or "media" refers to liquid, semi-solid, or solid media used to support bacterial cell growth in a non-native environment. Further, by culture media is meant a sterile solution that is capable of sustaining and/or promoting the division or survival of such cells. Suitable culture media are known to one of skill in the art, as discussed herein. The media components may be obtained from suppliers other than those identified herein and may be optimized for use by those of skill in the art according to their requirements. Culture media components are well known to one of skill in the art and concentrations and/or components may be altered as desired or needed.

In certain embodiments, sequences of the present invention, including primer sequences, target sequences and internal amplification control (IAC) sequences may be identical to the sequences provided here in or comprise less than 100% sequence identity to the sequences provided herein. For instance, primer sequences, target sequences or IAC sequences of the present invention may comprise 90-100% identity to the sequences provided herein.

The terms "identical" or "percent identity," in the context of two or more nucleic acids or sequences, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., the NCBI web site found at ncbi.nlm.nih.gov/BLAST/or the like). Such sequences are then referred to as "substantially identical." This definition also refers to, or applies to, the compliment of a particular sequence. The definition may also include sequences that have deletions, additions, and/or substitutions. To compensate for gene sequence diversity and to target multiple gene variants of the same genes, degenerated primer pairs (1-2 bases or approximately 5-10% alterations) are allowed.

As used herein, the term "nucleic acid" refers to a single or double-stranded polymer of deoxyribonucleotide bases or ribonucleotide bases read from the 5' to the 3' end, which may include genomic DNA, target sequences, primer sequences, or the like. In accordance with the invention, a "nucleic acid" may refer to any DNA or nucleic acid to be used in an assay as described herein, which may be isolated or extracted from a biological sample. The term "nucleotide sequence" or "nucleic acid sequence" refers to both the sense and antisense strands of a nucleic acid as either individual single strands or in the duplex. The terms "nucleic acid segment," "nucleotide sequence segment," or more generally, "segment," will be understood by those in the art as a functional term that includes genomic sequences, target sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

The term "gene" refers to components that comprise bacterial DNA or RNA, cDNA, artificial bacterial DNA polynucleotide, or other DNA that encodes a bacterial peptide, bacterial polypeptide, bacterial protein, or bacterial RNA transcript molecule, introns and/or exons where appropriate, and the genetic elements that may flank the coding sequence that are involved in the regulation of expression, such as, promoter regions, 5' leader regions, 3' untranslated regions that may exist as native genes or transgenes in a bacterial genome. The gene or a fragment thereof can be subjected to polynucleotide sequencing methods that determines the order of the nucleotides that comprise the gene. Polynucleotides as described herein may be complementary to all or a portion of a bacterial gene sequence, including a promoter, coding sequence, 5' untranslated region, and 3' untranslated region. Nucleotides may be referred to by their commonly accepted single-letter codes.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular electrode is disclosed and discussed and a number of modifications that can be made to the electrode are discussed, specifically contemplated is each and every combination and permutation of the electrode and the modifications that are possible unless specifically indicated to the contrary. Thus, if a class of electrodes A, B, and C are disclosed as well as a class of electrodes D, E, and F and an example of a combination electrode, or, for example, a combination electrode comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures that can perform the same function which are related to the disclosed structures and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Methods and Compositions for Detection of Virulent Strains of *Salmonella*

Methods of Quantifying Microorganisms

Foodborne illnesses significantly impact society, not only with respect to health, but also healthcare costs. The CDC has estimated that each year about 1 in 6 Americans (or 48 million people) gets sick, 128,000 are hospitalized, and 3,000 die of foodborne diseases (see www.cdc.gov/foodsafety/facts.html). It has also been estimated that foodborne illnesses contribute to $152 billion in health-related expenses each year in the US, particularly for bacterial infections caused by strains of *Campylobacter, Salmonella, Listeria monocytogenes*, and *E. coli*.

Disclosed herein are methods for quantifying an amount of target nucleic acid in a sample, enabling estimation of initial target (i.e., microorganism) concentration in the test sample, the method comprising: providing a sample comprising at least one target nucleic acid; dividing the sample of step a) into at least two containers; amplifying the target nucleic acid in each container by exposing each sample to a different set of primers in uniplex or multiplex under conditions suitable for nucleic acid amplification, wherein each set of primers comprises a forward and reverse primer, and further wherein at least one primer in each primer set has varying specificity for the target nucleic acid compared to the others, thereby creating an amplification product; exposing the amplification product to a probe which is specific for the target nucleic acid; and determining which of the containers showed a detectable level of amplification using the probe, thereby quantifying the amount of target nucleic acid in the sample. The same process can be performed in less number of container by using a multiplex 5'-nuclease real-time PCR approach. Importantly, the amount of target nucleic acid is determined without the use of any external standard curve. The amount of nucleic acid present can be used for estimating the amount of target organism present in the test sample.

By "target nucleic acid" is meant a nucleic acid specific for a microorganism, such as a pathogen, present in a sample and in need of detection. The sample can be taken from any source in which microorganisms need to be quantified. The methods described herein may be used to test a multitude of biological samples, for example, food products. In one embodiment, a biological sample may be meat such as beef, beef stew meat, beef trimmings, chicken, turkey, fish, shellfish, eggs, or the like. A biological sample may also include produce such as various vegetables and fruits, such as alfalfa sprouts, spinach, lettuce, or juices from vegetables or fruits such as apple cider. As used herein, a "biological sample" or "sample" may also include clinical samples such as blood and blood parts including, but not limited to serum, plasma, platelets, or red blood cells; sputum, mucosa, tissue, cultured cells, including primary cultures, explants, and transformed cells; biological fluids, stool, and urine. A biological sample may also include sections of tissues such as biopsy and autopsy samples, and frozen sections taken for histologic purposes. A biological sample may be obtained from a eukaryotic organism, for example a mammal, including humans, cows, pigs, chickens, turkeys, ducks, geese, dogs, goats, and the like. Any tissue appropriate for use in accordance with the invention may be used, for instance, skin, brain, spinal cord, adrenals, pectoral muscle, lung, heart, liver, crop, duodenum, small intestine, large intestine, kidney, spleen, pancreas, adrenal gland, bone marrow, lumbosacral spinal cord, or blood.

Further contemplated are samples from water, such as naturally occurring water such as rivers, streams, lakes, oceans, or ponds; or manmade bodies of water, such as agricultural bodies of water, holding ponds, holding tanks, sludge, sewage water, spray fields, wastewater treatment facilities, etc.

In some embodiments, methods of the present invention may comprise the steps of: i) enriching a bacterial concentration in a test sample by incubating the sample aerobically at approximately 42° C., for instance 37° C., 38° C., 39° C., 40° C., 41° C., 42° C., 43° C., 44° C., or 45° C. in an enrichment media such as described herein; ii) isolating DNA from the enriched sample; and iii) detecting sample DNA using the specific primer sets as described herein.

During the sample enrichment step, a biological sample, such as a food sample or other clinical sample, may be collected and diluted in appropriate buffer or media such as water, saline, brain heart infusion broth (BHI), tryptic soy broth (TSB), or sterile Buffered Peptone Water (BPW), among others. Media useful for culture or enrichment of STECs, *Salmonella*, or other food pathogens in food samples would be known by one of skill in the art. Exemplary media in accordance with the invention may include, but are not limited to, BHI, TSB, mTSB, and buffered peptone water (BPW) broth. In some embodiments, a sample as described herein may be diluted at any stage in a desired buffer or solution, for example 1:10, 1:9, 1:8, 1:7, 1:6, 1:5, 1:4, 1:3, 1:2, or 1:1.

The samples disclosed herein can be divided into containers or tubes for quantification purposes. The samples can be divided into two, three, four, five, six, seven, eight, nine, ten, or more containers or tubes. Into each container or tube, a different set of primers with varying amplification efficiency for the target nucleic acid, when compared to the other set of primers, can be added. The same process can be performed by using less number of tubes using a multiplex 5'-nuclease real-time PCR assays. In this way, one can determine which primers can, and which primers cannot, amplify the sample. Because each set of primers has a different amplification efficiency, one can easily determine the starting quantity of the sample present. The same probe can be used in each container, or different probes can be used, as long as the skilled artisan adjusts for different hybridization efficiencies of different probes.

These containers or tubes can be formed of any material known to those of skill in the art for forming dilutions, or for storing or testing samples. Microbiological culture bottles, tubes, syringes, vials, vessels, and the like (e.g., enrichment vessels and detection vials) suitable for use with the presently disclosed methods, systems, and devices can, in some embodiments, be made of glass or plastic. In some applications, a multilayered plastic is desirable to control gas permeability. In those embodiments wherein the microbiological culture vessel is made of multilayered plastic, the a sample, then determine if that level is above or below an acceptable reference level. For example, the Food Standards Committee in Australia gives the following information (available at Australia's Food Standard website, herein incorporated by reference in its entirety).

TABLE 1

Guideline levels for determining the microbiological quality of ready-to-eat foods

| Test | Microbiological Quality (CFU per gram) | | | |
|---|---|---|---|---|
| | Satisfactory | Marginal | Unsatisfactory | Potentially Hazardous |
| Standard Plate Count | | | | |
| Level 1. | $<10^4$ | $<10^5$ | $\geq 10^5$ | |
| Level 2. | $<10^6$ | $<10^7$ | $\geq 10^7$ | |
| Level 3. | N/A | N/A | N/A | |
| Indicators | | | | |
| *Enterobacteriaceae** | $<10^2$ | $10^2$-$10^4$ | $\geq 10^4$ | |
| *Escherichia coli* | $<3$ | 3-100 | 100 | ** |
| Pathogens | | | | |
| Coagulase +ve Staphylococci | $<10^2$ | $10^2$-$10^3$ | $10^3$-$10^4$ | $\geq 10^4$ SET +ve |
| *Clostridium perfringens* | $<10^2$ | $10^2$-$10^3$ | $10^3$-$10^4$ | $\geq 10^4$ |
| *Bacillus cereus* and other pathogenic *Bacillus* spp | $<10^2$ | $10^2$-$10^3$ | $10^3$-$10^4$ | $\geq 10^4$ |
| *Vibrio parahaemolyticus* # | $<3$ | $<3$-$10^2$ | $10^2$-$10^4$ | $\geq 10^4$ |
| Campylobacter spp | not detected in 25 g | | | detected |
| Salmonella spp | not detected in 25 g | | | detected |
| *Listeria monocytogenes* | not detected in 25 g | detected but $<10^{2\ddagger}$ | | $\geq 10^2$ ## |

*Enterobacteriaceae testing is not applicable to fresh fruits and vegetables or foods containing these.
**Pathogenic strains of E. Coli should be absent.
V. parahaemolyticus should not be present in seafoods that have been cooked. For ready-to-eat seafoods that are raw, a higher satisfactory level may be applied ($<10^2$ cfu/g).
The potentially hazardous level of V. parahaemolyticus relates to Kanagawa-positive strains.
‡Foods with a long shelf life stored under refrigeration should have no L. monocytogenes detected in 25 g.
The detection of L. monocytogenes in ready-to-eat foods prepared specifically for "at risk" population groups (the elderly, immunocompromised and infants) should also be considered as potentially hazardous.
N/A—SPC testing not applicable. This applies to foods such as fresh fruits and vegetables (including salad vegetables), fermented foods and foods incorporating these (such as sandwiches and filled rolls).

bottle may be injection or blow molded and have inner and outer layers of polyester, polypropylene, polyethylene, polyvinyl chloride, polycarbonate, polyethylene terephthalate (PET), cyclic olefin copolymer (COC), or any copolymer or mixture thereof separated by an intermediate layer of nylon, ethylene vinyl alcohol (EVOH), polyethylene vinyl alcohol, or copolymers or mixtures thereof. However, it is understood that the vessel may not be multilayered in other embodiments and formed using similar techniques (e.g., injection or blow molding). In some applications, the vessel components may be treated with a surface coating or chemical methods to control vessel/sample interactions or physical properties. In some embodiments, the vessel can be transparent to visible radiation, although, in particular embodiments, such transparency is not required. Additionally, in some embodiments, the presently disclosed vessels can be adaptable to sterilization. Further, in some embodiments, the vessel is suitable for aerobic or anaerobic culture. In one embodiment, the vessel is gas permeable. In addition, the vessel may include a constant wall thickness along its length, which may enhance pelleting and optical analysis.

One of skill in the art can determine what reference levels to use, and what acceptable ranges are for food and water safety purposes. The methods disclosed herein allow the skilled artisan to determine a range of a pathogen present in Similar information can be found for the UK at their government website for Food Safety, herein incorporated by reference in its entirety.

Isolation and Amplification of DNA

During the DNA isolation step as described herein, DNA from an enriched sample may be isolated using any method available as would be known by one of skill in the art. In one embodiment, a commercially available kit, such as PrepMan® Ultra Sample Preparation Reagent (Applied Biosystems, Life Technologies) may be used to isolate DNA. According to one embodiment, suspended food particles may be separated from the media, for instance through filtration or centrifugation of the enriched sample, for example at 100×g. The obtained supernatant may then be used for DNA isolation as described herein.

Methods such as polymerase chain reaction (PCR and RT-PCR) and ligase chain reaction (LCR) may be used to amplify nucleic acid sequences directly from genomic material, such as genomic DNA, mRNA, cDNA, or from genomic libraries, or cDNA libraries.

The probe used to detect the target nucleic acid can be any probe known to those of skill in the art used in nucleic acid detection. The probe can be a single probe or a dual-labeled probe, such as those found in FRET systems. Detectable labels may include, but are not limited to, radiolabels, fluorochromes, including fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxy fluorescein (5-FAM) or N,N,N',N'-tetramethyl-6-carboxyrho-damine (TAMRA); radioactive labels such as 32P, 35S, and 3H), and the like. In some embodiments, a detectable label may involve multiple steps (e.g., biotin-avidin, hapten-anti-hapten antibody, and the like). A primer useful in accordance with the invention may be identical to a particular bacterial target nucleic acid sequence and different from other bacterial sequences.

The probes selected and/or utilized by the methodologies of the invention can provide sensitivity and/or specificity of more than 95%, 96%, 97%, 98%, 99%, or 100%. In some embodiments, sensitivity and specificity depends on the hybridization signal strength, number of probes used, the number of potential cross-hybridization reactions, the signal strength of the mismatch probes, if present, background noise, or combinations thereof.

The oligonucleotide probes can each be from about 5 to about 100 nucleotides, from about 10 to about 50 nucleotides, from about 15 to about 35 nucleotides or from about 20 to about 30 nucleotides. In some embodiments, the probes are at least 5-mers, 6-mers, 7-mers, 8-mers, 9-mers, 10-mers, 11-mers, 12-mers, 13-mers, 14-mers, 15-mers, 16-mers, 17-mers, 18-mers. 19-mers, 20-mers, 21-mers, 22-mers, 23-mers, 24-mers, 25-mers, 26-mers, 27-mers, 28-mers, 29-mers, 30-mers, 31-mers, 32-mers, 33-mers, 34-mers, 35-mers, 36-mers, 37-mers, 38-mers, 39-mers, 40-mers, 41-mers, 42-mers, 43-mers, 44-mers, 45-mers, 46-mers, 47-mers, 48-mers, 49-mers, 50-mers, 51-mers 52-mers, 53-mers, 54-mers, 55-mers, 56-mers, 57-mers, 58-mers, 59-mers, 60-mers, 61-mers, 62-mers, 63-mers, 64-mers, 65-mers, 66-mers, 67-mers, 68-mers, 69-mers, 70-mers, 71-mers, 72-mers, 73-mers, 74-mers, 75-mers, 76-mers, 77-mers, 78-mers, 79-mers, 80-mers, 81-mers, 82-mers, 83-mers, 84-mers, 85-mers, 86-mers, 87-mers, 88-mers, 89-mers, 90-mers, 91-mers, 92-mers, 93-mers, 94-mers, 95-mers, 96-mers, 97-mers, 98-mers, 99-mers, 100-mers or combinations thereof As described above, each primer set has a different amplification efficiency. Each primer set has a forward and a reverse primer. The amplification can be done in multiplex form, so that more than one set of primers is present in a container. The forward and reverse primers can have different amplification efficiencies, which is based on the specificity of the primer for the target. For example, one primer set can be 100% complementary to the target. When this is the case, there are no mismatches, and the primer is very efficient at amplifying the target, even at lower levels. Primers can also have less than 100% complementarity, so that they comprise 1, 2, 3, 4, 5, 6, 7, or more mismatches. Put another way, they can have 80, 85, 90, 95, 96, 97, 98, or 99% identity, or more or less or in between these values. These mismatches can compromise their amplification efficiency. The skilled artisan will know what the amplification efficiency is of each individual primer pair, and can therefore determine the concentration of target nucleic acid that each primer pair will be able to amplify. Therefore, when different containers have the different amounts of target nucleic acid and sample is amplified by pre-selected different nucleic acid primer sets with different efficiencies, one skill in the art can determine which containers were successfully amplified or which probe in a multiplex reaction generated positive amplification signal, and therefore extrapolate the quantity of the starting nucleic sample.

In some embodiments, the primers are not labeled, and the amplicons may be visualized, detected, and/or analyzed following their melting temperature, for example by generation of melt curve assays or plots. In other embodiments, the RNA can be isolated, reverse transcribed, and amplified in multiplex real-time PCR reaction facilitation target quantification and differentiation of live and dead cells. In other embodiments, an amplicon may be visualized according to size, e.g., using agarose gel electrophoresis. In some embodiments, ethidium bromide staining of the PCR amplicons following band presence or absence when tested using pre-selected different nucleic acid primer sets with different efficiencies. Such an approach may be referred to as endpoint PCR. Conventional endpoint PCR, while suitable for amplification and detection of a target DNA or sequence, may require extensive sample enrichment time due to the higher copy number of target DNA molecules needed for detection. This translates to a higher number of target cells, which, in turn, translates to longer enrichment times. In some embodiments, the primers of the invention may be radiolabeled, or labeled by any suitable means (e.g., using a non-radioactive fluorescent tag), to allow for rapid visualization of amplicons of different sizes following an amplification reaction without any additional labeling step or visualization step.

In accordance with the invention, a PCR assay as described herein, may be multiplexed in order to combine multiple reactions into a single assay. For example, a multiplex assay may enable amplification of multiple target sequences using a number of PCR primer pairs, such as one or more primers set forth in the Examples. One skilled in the art will understand that the reaction conditions for each individual reaction in a multiplex assay will necessarily be similar in order to achieve efficient amplification of each target. Optimization or other testing of each individual primer pair may be necessary. For the development of a multiplex PCR assay such as described herein, a large number of primer pairs have to be tested for each target in order to determine the optimum primer that will produce the best result. Out of multiple PCR primers that work for a particular multiplex assay, a final set of primer pairs for a multiplex assay may be selected based on specific criteria, including, but not limited to, (1) PCR primer amplification efficiency; and (2) amplicon size.

A PCR assay may include a number of reagents and components, including a master mix and nucleic acid dye or intercalating agent. In some embodiments, an exemplary PCR master mix may contain template genomic material, such as DNA or RNA, PCR primers, probes salts such as $MgCl_2$, a polymerase enzyme, and deoxyribonucleotides. One of skill in the art will be able to identify useful components of a master mix in accordance with the present invention. In one embodiment, a master mix with an intercalating dye or a probe master mix may be used.

During real-time PCR detection, PCR may be performed in any reaction volume, such as 10 μL, 20 μL, 30 μL, 50 μL, 100 μL, or the like. Reactions may be performed singly, in duplicate, or in triplicate. PCR thermal cycling conditions are well-known in the art and vary based on a number of factors. As described herein, an exemplary two-step or three-step amplification protocol based on manufacturer's instructions may include, for example, an initial denaturation at 94° C. for 10 min, 40 cycles of 94° C. for 30 s, 60° C. for 45 s; and a melt curve step may be performed at the end of the PCR (from 60° C. to 95° C., with gradual temperature increments of 0.04-0.1° C./s). A amplification plot can be plotted for probe-based real-time PCR assay.

Melt curve plots may be prepared by plotting the negative derivative of fluorescence (−Rn) versus temperature. Any thermal cycling program may be designed as appropriate for use with the particular primers for detection of particular bacterial species as would be understood by one of skill in the art.

In addition, a reaction control may be used, such as an IAC, in order to avoid false negative results and thereby increase the reliability of an assay. The use of an IAC in a reaction provides assurance that a negative result for a target is truly a negative result rather than due to a problem or break-down in the reaction. Because the signal for the IAC should always be generated, even when the target signal is not generated (i.e., the target organism or DNA is not present in the sample), this would indicate that a negative target signal is indeed a negative result. An IAC may be useful in diagnostic assays because food matrices may harbor inhibitory components that may interfere with PCR amplification, leading to false negative results. 16S rRNA gene sequence or any other gene sequence or laboratory-designed short oligonucleotide sequence can be used as an IAC in a PCR reaction. Those skilled in the art can select suitable IAC needed for the PCR reaction.

Short oligonucleotides such as an IAC molecule as described herein may be amplified at a much higher amplification efficiency (>100%) and thus may be preferentially amplified in a multiplex PCR reaction. To overcome this issue, an IAC molecule may be added to a multiplex reaction at the lowest possible concentration (10-20 fg), facilitating preferential amplification of the desired target DNA.

In accordance with the invention, IAC oligonucleotides, as described herein may be added to a PCR reaction or assay at any concentration suitable for the assay. In some embodiments, the concentration of an IAC may be very low, such as 10 fg or 100 fg per 10 µL reaction, for example, 1 fg, 2 fg, 3 fg, 4 fg, 5 fg, 10 fg, 20 fg, 30 fg, 50 fg, 75 fg, 85 fg, 90 fg, or 100 fg per 10 µL reaction. Lower concentrations of IAC oligonucleotides may allow preferential amplification of pathogenic genomic DNA or target sequences to be detected, and in the process, the size of the IAC peak generated in a multiplex reaction may be smaller when compared with other peaks. In the case of a negative control, the size of the IAC peak may be bigger because all of the primers are available for its amplification.

Modification of Nucleic Acids

Any number of methods well known to those skilled in the art can be used to isolate and manipulate a DNA molecule. For example, as previously described, PCR technology may be used to amplify a particular starting DNA molecule and/or to produce variants of the starting DNA molecule. DNA molecules, or fragments thereof, can also be obtained by any techniques known in the art, including directly synthesizing a fragment by chemical means. Thus, all or a portion of a nucleic acid as described herein may be synthesized.

As used herein, the term "complementary nucleic acids" refers to two nucleic acid molecules that are capable of specifically hybridizing to one another, wherein the two molecules are capable of forming an anti-parallel, double-stranded nucleic acid structure. In this regard, a nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are known in the art and described by Sambrook, et al. (1989), and by Haymes et al. (1985).

Departures from complete complementarity are permissible, as long as the capacity of the molecules to form a double-stranded structure remains. Thus, in order for a nucleic acid molecule or a fragment of the nucleic acid molecule to serve as a primer or probe, such a molecule or fragment need only be sufficiently complementary in sequence to be able to form a stable double-stranded structure under the particular solvent and salt concentrations employed.

Appropriate stringency conditions that promote DNA hybridization are well known to one of skill in the art and may include, for example, 6× sodium chloride/sodium citrate (SSC) at about 45° C., followed by a wash of 2×SSC at 50° C. The salt concentration in the wash step may be selected from a low stringency of approximately 2×SSC at 50° C. to a high stringency of about 0.2×SSC at 50° C. The temperature in the wash step may be increased from low stringency conditions at room temperature, about 22° C., to high stringency conditions at about 65° C. The temperature and/or salt conditions may be varied as appropriate for optimum results. In accordance with the invention, a nucleic acid may exhibit at least from about 80% to about 100% sequence identity with one or more nucleic acid molecules as described herein, for example, at least from about 80%, about 85%, about 90%, about 95%, about 98%, about 99%, or about 100% sequence identity. One skilled in the art will understand that stringency may be altered as appropriate to ensure optimum results.

Kits and Specific Nucleic Acids

Also disclosed herein is a kit. The kit can comprise primers for the quantification of a target nucleic acid in a sample. The kit can also comprise two or more containers. In one example, each container comprises appropriate reagents for nucleic acid amplification, including a set of primers, wherein each primer set comprises a forward and a reverse primer, and further wherein each primer set in each container differs from at least one other primer set in one other container by 1, 2, 3, 4, or 5 nucleotides. The kit can also comprise a probe specific to the target nucleic acid. The kit can also comprise components for sample collection, such as means to obtain a sample, or to dilute the sample, or to store the sample. The kit can comprise any of the other compositions disclosed herein.

The invention further provides diagnostic reagents and kits comprising one or more such reagents or components for use in a variety of diagnostic assays, including for example, nucleic acid assays, e.g., PCR or RT-PCR assays. Such kits may preferably include at least a first primer pair as described herein, and means for detecting or visualizing amplification of a target sequence. In some embodiments, such a kit may contain multiple primer pairs as described herein for the purpose of performing multiplex PCR or RT-PCR for the detection of multiple target sequences. Primer pairs may be provided in lyophilized, desiccated, or dried form, or may be provided in an aqueous solution or other liquid media appropriate for use in accordance with the invention.

Kits may also include additional reagents, e.g., PCR components, such as salts including $MgCl_2$, a polymerase enzyme, and deoxyribonucleotides, and the like, reagents for DNA or RNA isolation, or enrichment of a biological sample, including for example media such as water, saline, BHI, TSB, BPW, or the like, as described herein. Such reagents or components are well-known in the art. Where appropriate, reagents included with such a kit may be provided either in the same container or media as the primer pair or multiple primer pairs, or may alternatively be placed in a second or additional distinct container into which the additional composition or reagents may be placed and suitably aliquoted. Alternatively, reagents may be provided in a single container means.

Disclosed herein are specific primers for amplifying the nucleic acid target from the sample. For example, when the target microorganism is *Salmonella*, the following probes can be used (sequences are found below in Example 1). One set of primers can comprise SEQ ID NOS: 1 and 2 (1 is forward, 2 is reverse). A second set of primers can comprise SEQ ID NOS: 4 and 5 (4 is forward, 5 is reverse). A third set of primers can comprise SEQ ID NOS: 7 or 8 and 9 (7 and 8 are both forward and can be used simultaneously or either one can be used independently, 9 is reverse). A fourth set of primers comprising SEQ ID NOS: 11 and 12 (11 is forward, 12 is reverse). A fifth set of primers comprising SEQ ID NOS: 14 and 15 (14 is forward, 15 is reverse). Each forward primer (SEQ ID NOS: 1, 4, 7, 8, 11 and 14) have different amplification efficiencies. Also disclosed for use are probes comprising SEQ ID NOS 3, 6, 10, and 13. These primers, probes, and corresponding amplification targets can be found in Table 2. Also disclosed are primers and probes comprising 80% or more identity to these primers and probes. Put another way, these primers and probes can have 1, 2, or 3 or more additions, deletions, or substitutions and are still contemplated for use with the methods and kits disclosed herein.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, the temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: Development of Live *Salmonella* Detection and Quantification Assay

*Salmonella* strains are the most frequent cause of foodborne illness. Despite the United States Department of Agriculture (USDA), Food Safety Inspection Services (FSIS) best efforts the rate of *salmonellosis* in the US is above public health goals. In the US, *Salmonella* is estimated to cause 1.35 million foodborne illnesses, with 26,500 hospitalizations and results in 420 deaths annually. Strains of *Salmonella* are attached to the exterior surface (i.e., hide, feather) of the food animals, and they often colonize their internal organs. The USDA, FSIS recognizes the threat posed by *Salmonella* in raw meat and has set performance standards for protecting public health. The USDA, FSIS *Salmonella* performance standards permits a number of samples within a sample set that can test positive for the presence of *Salmonella* spp. However, the USDA, FSIS *Salmonella* performance standards does not address the actual *Salmonella* concentration levels (CFU/g) in the samples that tests positive after enrichment process. In other words, a raw meat sample that tests positive by a PCR-based method may contain anywhere between one to $10^6$ CFUs of *Salmonella* cells in 25/325 g of meat sample. Samples with different *Salmonella* contamination level poses different health risks. Infective dose of *Salmonella* strains varies, and the consumption of different amounts of viable *Salmonella* cells is associated with varying disease outcomes (Blaser & Newman, 1982). The exact number of *Salmonella* cells needed to cause illness depends on multiple factors including (i.e., serotype, strain, host susceptibility, and iron status) (Blaser & Newman, 1982; Ponder, 2017). Nevertheless, from a public health perspective, the food samples contaminated with higher concentrations of *Salmonella* pose a more serious concern than samples contaminated with a low concentration of *Salmonella*.

Currently, regulatory agencies and other testing laboratories rely on the combination of selective enrichment, real-time PCR, and culture-based methods for specific detection of *Salmonella* in food samples (Lee et al., 2015). One of the limitations of a real-time PCR-based *Salmonella* detection assay using DNA isolated from enrichments is its inability to quantify *Salmonella* load in the original sample. Most probable number (MPN)-based methods are used for the enumeration of *Salmonella* in food samples (Hussong et al., 1984; Santos et al., 2005). As culture and MPN-based *Salmonella* detection methods require a longer enrichment period, it makes these methods undesirable for the food industry and regulatory agencies. Therefore, a rapid method for detection and estimation of *Salmonella* load, with a shorter turnaround time that quickly provides actionable results is needed.

The FSIS, with its partners, is targeting a 25% reduction in *salmonellosis* cases. To reach this goal, improved *Salmonella* detection methods with the ability to quantify *Salmonella* from enrichments are needed. Such a method will strengthen existing FSIS performance standard and surveillance programs. Further, improved *Salmonella* detection methods will be useful for the processors to understand and elucidate how often a meat product is contaminated with different concentrations of *Salmonella*. Understanding the true spectrum of *Salmonella* load in positive samples will allow the industry to better understand the problem and thereby apply suitable intervention measures.

The approach disclosed herein takes advantage of differing PCR amplification efficiencies created by introducing mismatch in the primer sequence for estimating the bacterial load in the biological samples. That is, the primer sequence exactly matches a target gene are amplified at a high amplification efficiency, and can detect a very low concentration of target organism (1 $\log_{10}$ CFU) in a test sample. Whereas primers designed with an increasing number of mismatches resulting in a lower amplification efficiency, which in turn enables the detection of different concentrations of the target organisms. As the amplification is carried out with primers with mismatches, the assay specificity is maintained by the use of a highly specific dual-labeled hydrolysis probe designed to detect the specific target.

Disclosed herein are methods that allow for the specific detection as well as estimation of target organism load in the test samples. This approach is useful for the food and diagnostic industry. The detection and quantification/estimation information generated by this approach will enable the food industry to divert food samples to the cooked product stream and optimize the cooking process to reach 5 $\log_{10}$ reductions, and help the industry avoid outbreaks.

The methods and assays disclosed herein directly detect and quantify the target organism. Further, the same approach can be used for the standardization of rapid quantitation/estimation methods for any target organism of interest without the need to build regression curves. These assays and methods can be adopted by a significant number of meat (or other foodstuffs) producers wishing to quickly identify high levels of contaminating microorganisms that require meat to be diverted to different processing streams using thermal lethality treatments.

Overview of developed method: Multiple *Salmonella* gene targets have been used in the past to develop PCR-based methods for the detection of *Salmonella*. PCR assays targeting a single gene are commonly used for the specific detection of *Salmonella* (i.e., InvA). A previous study demonstrated that single-gene PCR detection of *Salmonella* is not accurate (Liu et al., 2018). The target gene may be missing in some strains resulting in false-negative results. Therefore, building on that previous study, a three-gene multiplex real-time PCR approach was used to detect and quantify/estimate live *Salmonella* cells.

Primer and Probes: *Salmonella* quantification assay was standardized by making improvements to a previous assay. Mutations in the forward primers sequence targeting the stn and fimA genes were added to reduce the primer's amplification efficiency. Dula-labeled hydrolysis probe sequence for the stn and fimA was designed using primer3 software. New primers with mutations with their respective probes were tested for their ability to perform in the multiplex assay. Selected primer pairs and probe sequences are listed in Table 1. Previously, published primer and probe sequence targeting the bacterial conserved 16S rRNA gene sequence was used as an internal amplification control.

TABLE 2

Primer and probe used for real-time PCR assay.

| Primer | Sequence (5'-3') | Product (bp) |
|---|---|---|
| stn-1F | GCC ATG CTG TTC GAT ATA (SEQ ID NO: 1) | 100 |
| stn-1R | GGATCAGTTGGAGGCGATTT (SEQ ID NO: 2) | |
| stn-probe | HEX-GTCCCGTCAGCTTTGGTCGT-ZEN/IBFQ (SEQ ID NO: 3) | |
| *Salmonella*-F | CGGTGGGTTTTGTTGTCTTC (SEQ ID NO: 4) | 237 |
| *Salmonella*-R | TCATCGCACCGTCAAAGGA (SEQ ID NO: 5) | |
| Inv F | CCAGTTTATCGTTATTACCAAAGG (SEQ ID NO: 14) | 200 |
| Inv R | ATCGCACCGTCAAAGGARC (SEQ ID NO: 15) | |
| Sal-invA-SO-WH probe | 6-FAM-CTCTGGATGGTATGCCCGGTAAACA-ZEN/IAFQ (SEQ ID NO: 6) | |
| fimA-F3-225F | GCAGGTGCCTTTCTCCATT (SEQ ID NO: 7) | 243 |
| fimA-F11-225F | GCAGGTGCCTTTATCCATT (SEQ ID NO: 8) | |
| fimA-225R | AGCGTATTGGTGCCTTCAAC (SEQ ID NO: 9) | |
| fimA-probe | CAL Fluor Red 610-CTGGCTGTCTCCTCTGCG-BHQ-2 (SEQ ID NO: 10) | |
| 16SRna-F | CCTCTTGCCATCGGATGTG (SEQ ID NO: 11) | 99 |
| 16SRna-R | GGCTGGTCATCCTCTCAGACC (SEQ ID NO: 12) | |
| 16S rRNA Probe | CY5-GTGGGGTAACGGCTCACCTAGGCGAC-TAO/IBRQ (SEQ ID NO: 13) | |

RNA isolation: Overnight *Salmonella* ATCC 14028 culture was serially diluted in 9 mL phosphate buffer saline. RNA from 1 mL of serial dilution was isolated using Quick-RNA MicroPrep Kit (Zymo Research) following the manufacturer's instructions.

Real-time PCR assay: One microliter of isolated RNA without any dilution was used for the assay. Reverse transcript and multiplex 5'-nuclease assays were performed in the same reaction tube using a QuantiNova Multiplex RT-PCR Kit (Qiagen) following the manufacturer's instruction. The real-time PCR protocol used was as follows: 50° C.—10 min (reverse transcription), 95° C. —120 s, and forty cycles of 95° C.—5 s, 60° C.—30 s.

Results:
  The invA primer pair was the most efficient and can detect 2-8 log CFU.
  The fimA primer pair was able to detect 3-8 log CFU.
  The stn primer pair detected 5-8 log CFU.
  RNA isolated from heat-treated *Salmonella* dead samples showed no amplification

TABLE 3

Limit of detection and Cq value obtained from the serially diluted *Salmonella* ATCC 14028 culture.

| Salmonella 14028 | Real-time PCR Cq-values | | |
|---|---|---|---|
| Log CFU | InvA | FimA | Stn |
| 8.0 | 17.0 | 15.2 | 24.6 |
| 7.0 | 20.8 | 18.3 | 28.9 |
| 6.0 | 24.7 | 24.7 | 33.0 |
| 5.0 | 28.7 | 28.2 | 36.3 |
| 4.0 | 30.0 | 29.7 | No amplification |
| 3.0 | 31.1 | 30.3 | No amplification |
| 2.0 | 35.04 | No amplification | No amplification |

Data Interpretation: Each food processing facility can set its own cutoff levels based on data collected from the multiplex assay. For example, ready-to-eat food samples showing low contamination levels by invA primer can be rejected or diverted for reprocessing. Poultry processing facilities have a higher prevalence of *Salmonella* and are not considered an adulterant in raw products. These facilities can define their microbiological criteria based on PCR signals from the stn and fimA primer pair. Further, a standard curve for the invA gene can be constructed using spiked food samples and can be used to estimate *Salmonella* load in the specific food samples.

Benefits of *Salmonella* quantification assay version 2: Compared to version one, the multiplex PCR approach drastically reduces the number of reaction tubes and simplifies the process. The assay is performed using RNA, enabling the detection of only live *Salmonella* cells. Thus, eliminating any amplification from dead cells. Reverse transcription and the 5'-nuclease assay are performed in the same reaction tube. Therefore, reducing the number of steps involved in the assay.

The assays target three *Salmonella* genes in a multiplex reaction, further increasing the specificity of the *Salmonella* quantification/estimation assay. This assay allows processors to rapidly estimate *Salmonella* contamination levels in beef and poultry products and help them decide their course of action, thereby reducing recalls.

Example 2: Methods and Compositions for Determining Microorganism Presence and Concentration Using PCR Primers of Varying Amplification Efficiencies Introduction:

*Salmonella enterica* is a diverse species subdivided into six subspecies, consisting of over 2600 serotypes (Banerji et al. 2020). Therefore, selecting gene targets highly conserved among the *Salmonella* serotypes of concern is a critical step in developing a PCR assay for the detection and estimation of *Salmonella* levels in the food samples. The previous version of the *Salmonella* estimation assay relied on a multiplex TaqMan assay targeting three *Salmonella*-specific genes (i.e., invA, fimA, and stn). Where the invA primer was an unmodified primer and detected the low concentration of *Salmonella* in the test samples, in contrast, the fimA and stn primer pairs were modified by incorporating mismatches to the primer sequence to reduce the primer's amplification efficiency and enabled the detection of samples contaminated with a medium or high concentration of *Salmonella*, respectively.

The *Salmonella*-specific gene targets used in our work were previously validated for their specificity (Liu et al. 2018; Hu et al. 2021). However, the fimA primer pair without modifications was found to be not a reliable target for the detection of *Salmonella*, and in this study the primer pair failed to detect the *Salmonella infantis* strains, which is a big concern for the poultry industry. The lack of amplification for the fimA primer for the *Infantis* strains can be attributed to the fimA gene sequence diversity among *Salmonella* serotypes (Banerji et al., 2020). Hu et al. (2021) performed a whole genome sequence comparison of 143 *Salmonella* strains and reported the fimA gene as a questionable site for the development of PCR assay. The study further reported no mutation for the ttrR gene among all *Salmonella* strains analyzed in the study, making the ttrR gene target an ideal target for *Salmonella*-specific PCR assay.

Other important aspects of *Salmonella* detection and estimation assay for its industrial adoption are: (1) a short turnaround time which includes sample preparation, enrichment, DNA isolation, and real-time PCR, all performed to generate test results within an eight-hour workday; (2) ease of performing the assay, e.g., avoid use of long DNA isolation protocols, assay ability to work with quick dirty lysis DNA isolation protocol, and directly use of isolated DNA without any dilution; (3) use of a *Salmonella* enrichment media which can neutralize trace levels of acid (i.e., peroxyacetic acid) used for sanitizing poultry in a processing plant. Promote the growth of slow-growing *Salmonella* strains and deter the growth of other bacteria present on poultry skin.

Therefore, the aim of the study was to standardize a simple and reliable method for the detection as well as estimation of *Salmonella* levels in poultry rinses.

Methods

Primer and Probes: Improved *Salmonella* detection and estimation assay was standardized by making one change to our previous multiplex TaqMan assay. The fimA primer and probe were replaced with published primer and probe targeting the ttrR gene (Table 1), which can detect all six *Salmonella enterica* subspecies (Zhang et al., 2013). Previously, published primer and probe sequence targeting the bacterial conserved 16S rRNA gene sequence was used as an internal amplification control (IAC) (USDA 2019).

TABLE 4

Primer and probe used for real-time PCR assay.

| Primer | Sequence (5'-3') | Product (bp) |
|---|---|---|
| Stn-F18 | GCCATGCTGTTCGATTATATA (SEQ ID NO: 1) | 100 |
| Stn-R2 | SGATCAKYTGGAGGCGATTT (SEQ ID NO: 16) | |
| stn-probe | HEX-GTCCCGTCAGCTTTGGTCGT-ZEN/IBFQ (SEQ ID NO: 3) | |

TABLE 4-continued

Primer and probe used for real-time PCR assay.

| Primer | Sequence (5'-3') | Product (bp) |
|---|---|---|
| ttrR-F | GATGTTYCTTAGCGCYTTACAGGC (SEQ ID NO: 17) | 216 |
| ttrR-R | CCGACMGCGTAATATTTGGCTGAC (SEQ ID NO: 18) | |
| ttrR-probe | CAL Fluor Red 610-CGTCRGTGGATTWCCGTCGCCCT- BHQ-2 (SEQ ID NO: 19) | |
| 16SRna-F | CCTCTTGCCATCGGATGTG (SEQ ID NO: 11) | 99 |
| 16SRna-R | GGCTGGTCATCCTCTCAGACC (SEQ ID NO: 12) | |
| 16S rRNA Probe | CY5-GTGGGGTAACGGCTCACCTAGGCGAC-TAO/IBRQ (SEQ ID NO: 13) | |

Inoculated food samples: Chicken rinse was prepared by transferring a whole chicken to sterilized autoclave bags. Four hundred mL of PBS was added to each bag and were shaken for two minutes (FDA BAM 2020). The chicken rinse was transferred to autoclaved bottle and was tested for the presence of Salmonella using the standard method (USDA, 2019). Chicken rinses testing negative for Salmonella were used for the validation study. Before the experiment, 30 mL of chicken rinse was transferred to 50 mL sterile centrifuge tubes. These 30 mL chicken rinse samples were inoculated with a Salmonella strain at 1, 2, 3, and 4 log CFU/mL. All samples were inoculated in duplicates. To mimic industry testing practices, which involve overnight shipment of refrigerated samples to a private testing laboratory, inoculated samples were stressed by storing samples at 4° C. for 48 hours.

Sample enrichment: The inoculated samples were enriched using 15 mL of 3×neutralizing buffered peptone water (nBPW) (Hardy Diagnostics) supplemented with filter sterilized 15 mg/L novobiocin and 10 µM ferrous sulfate (Sigma). The enrichment media was tempered to 42° C. before adding it to the inoculated chicken rinse samples. The samples were enriched at 35±2° C., and one milliliter of enrichment was collected at the five and six-hour time points, and samples were used for DNA isolation.

DNA Isolation: Crude DNA from the enrichments was isolated using Extracta™ DNA Prep for PCR kit (Quantabio). Enrichments were centrifuged at 15,000×g for two minutes to harvest the bacterial cells. The supernatant was discarded, and the cell pellet was heated with 100 µl of lysis buffer at 100° C. for 10 minutes. Following the lysis steps, samples were incubated at room temperature for five minutes and then centrifuged at 12,000×g for two minutes. 60 µl of supernatant was transferred to a new Eppendorf tube containing 90 µl of neutralizing buffer. Thus obtained DNA samples were directly used for the real-time PCR assay without any dilution.

Real-time PCR: The multiplex TaqMan assay with the new ttrR primer and probe was initially optimized using pure culture Salmonella typhimurium ATCC 14028 DNA samples and KAPA probe force qPCR master mix (Kapa Biosystems) on a LC96 real-time PCR (Roche Diagnostics). The real-time PCR was performed using 21 of isolated DNA. The data for the real-time PCR assays were collected in the HEX (stn), CAL Fluor Red 610 (ttrR), and Cy5 (IAC) detection channels.

Results

The standardized multiplex assay with ttrR primer and probe amplified all the pure culture Salmonella DNA samples. The ttrR primer and probes amplified all the Salmonella infantis strains.

One milliliter of inoculated whole chicken rinses following a five- and six-hours enrichment period resulted in a DNA concentration between 200-300 ng/µl. The undiluted DNA samples showed reproducible amplification with the KAPA probe force qPCR master mix, demonstrating that the master mix can handle 400-600 ng of DNA in a 10 µl real-time PCR reaction. The direct use of isolated DNA for the real-time PCR assay enabled the reduction of the enrichment time as well as eliminated the sample processing time needed for diluting the DNA before the real-time PCR run.

The multiplex TaqMan assay targeting the stn, ttrR, and 16s rRNA genes detected all samples inoculated with Salmonella strains following a five-hours enrichment at 37±2° C. Data from the multiplex assay showed that the stn primer pair tested positive only for samples inoculated with 1 and 2 log CFU/30 mL and tested negative for samples inoculated with 3 and 4 log CFU/30 mL. The ttrR primers and probe only tested positive when the rinses were inoculated at higher levels (3-4 log CFU/30 mL or above). Therefore, it can be concluded that if the assay generates signals for the stn gene (HEX) and IAC (Cy5), then the samples are contaminated with a low level of Salmonella (1-2 log CFU/30 mL). If the samples generate signals for the ttrR gene (CAL Fluor Red 610), and IAC (Cy5), then the samples are contaminated with above 3 log CFU/30 mL of Salmonella.

The use of a rapid heat lysis-based DNA isolation protocol enabled completion of the DNA isolation in close to 30 minutes, setting up the real-time PCR reaction took around 30 minutes, and the real-time PCR run was completed in one hour. Thus, the assay developed in this study can be completed in seven hours, which includes time for sample enrichment, DNA isolation, and real-time PCR.

This real-time assay provides a result in simple terms (low or high contamination levels). This simple real-time PCR assay for the detection and estimation of Salmonella load can help the regulatory agencies and the food industry quickly identify Salmonella contamination samples and decide the implementation of the best-suited corrective measure based on the Salmonella load in the food samples (e.g., discard or divert for heat treatment).

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims.

REFERENCES

Anderson, A., Pietsch, K., Zucker, R., Mayr, A., Müller-Hohe, E., Messelhäusser, U., Sing, A., Busch, U., &

Huber, I. (2011). Validation of a Duplex Real-Time PCR for the Detection of *Salmonella* spp. In Different Food Products. *Food Analytical Methods*, 4(3), 259-267. https://doi.org/10.1007/s12161-010-9142-8

Blaser, M. J., & Newman, L. S. (1982). A Review of Human *Salmonellosis*: I. Infective Dose. *Reviews of Infectious Diseases*, 4(6), 1096-1106. https://doi.org/10.1093/clinids/4.6.1096

Hussong, D., Enkiri, N. K., & Burge, W. D. (1984). Modified agar medium for detecting environmental Salmonellae by the most-probable-number method. *Applied and Environmental Microbiology*, 48(5), 1026-1030.

Lee, K.-M., Runyon, M., Herrman, T. J., Phillips, R., & Hsieh, J. (2015). Review of *Salmonella* detection and identification methods: Aspects of rapid emergency response and food safety. *Food Control*, 47, 264-276. https://doi.org/10.1016/j.foodcont.2014.07.011

Liu, Y., Singh, P., & Mustapha, A. (2018). Multiplex high resolution melt-curve real-time PCR assay for reliable detection of *Salmonella*. *Food Control*, 91, 225-230. https://doi.org/10.1016/j.foodcont.2018.03.043

Ponder, M. A. (2017). The effects of food composition on foodborne illness infectious dose and host susceptibility. In J. B. Gurtler, M. P. Doyle, & J. L. Kornacki (Eds.), *Foodborne Pathogens: Virulence Factors and Host Susceptibility* (pp. 469-494). Springer International Publishing. https://doi.org/10.1007/978-3-319-56836-2_17

Santos, F. B. O., Li, X., Payne, J. B., & Sheldon, B. W. (2005). Estimation of most probable number *Salmonella* populations on commercial North Carolina turkey farms. *Journal of Applied Poultry Research*, 14(4), 700-708. https://doi.org/10.1093/japr/14.4.700

Singh, P., Liu, Y., Bosilevac, J. M., & Mustapha, A. (2019). Detection of Shiga toxin-producing *Escherichia coli*, stx1, stx2 and *Salmonella* by two high resolution melt curve multiplex real-time PCR. *Food Control*, 96, 251-259. https://doi.org/10.1016/j.foodcont.2018.09.024

Singh, P., & Mustapha, A. (2013). Multiplex TaqMan® detection of pathogenic and multi-drug resistant *Salmonella*. *International Journal of Food Microbiology*, 166(2), 213-218. https://doi.org/10.1016/j.ijfoodmicro.2013.07.023

USDA, FSIS. (2019). *Primer* and *Probe Sequences* and *Reagent Concentrations for non*-0157 *Shiga* Toxin-*Producing Escherichia coli* (*STEC*) *Real-Time PCR Assay*. *MLG 5C Appendix* 4.00. https://www.fsis.usda.gov/wps/wcm/connect/1d61852b-0b71-45e9-8914-8ff95af7aaa8/mlg-5-appendix-4.pdf?MOD=AJPERES

| SEQUENCES |
| --- |
| SEQ ID NO: 1 |
| GCCATGCTGTTCGATTATATA |
| SEQ ID NO: 2 |
| GGATCAGTTGGAGGCGATTT |
| SEQ ID NO: 3 |
| GTCCCGTCAGCTTTGGTCGT |
| SEQ ID NO: 4 |
| CGGTGGGTTTTGTTGTCTTC |
| SEQ ID NO: 5 |
| TCATCGCACCGTCAAAGGA |
| SEQ ID NO: 6 |
| CTCTGGATGGTATGCCCGGTAAACA |
| SEQ ID NO: 7 |
| GCAGGTGCCTTTCTCCATT |
| SEQ ID NO: 8 |
| GCAGGTGCCTTTATCCATT |
| SEQ ID NO: 9 |
| AGCGTATTGGTGCCTTCAAC |
| SEQ ID NO: 10 |
| CTGGCTGTCTCCTCTGCG |
| SEQ ID NO: 11 |
| CCTCTTGCCATCGGATGTG |
| SEQ ID NO: 12 |
| GGCTGGTCATCCTCTCAGACC |
| SEQ ID NO: 13 |
| GTGGGGTAACGGCTCACCTAGGCGAC |
| SEQ ID NO: 14 |
| CCAGTTTATCGTTATTACCAAAGG |
| SEQ ID NO: 15 |
| ATCGCACCGTCAAAGGAXC |
| SEQ ID NO: 16 |
| SGATCAKYTGGAGGCGATTT |
| SEQ ID NO: 17 |
| GATGTTYCTTAGCGCYTTACAGGC |
| SEQ ID NO: 18 |
| CCGACMGCGTAATATTTGGCTGAC |
| SEQ ID NO: 19 |
| CGTCRGTGGATTWCCGTCGCCCT |

What is claimed is:

1. An isolated primer pair comprising SEQ ID NOS: 1 and 2.

2. A primer pair comprising SEQ ID NOS: 1 and 16.

3. A nucleic acid probe for detecting an amplification product produced by the isolated primer pair of claim 1, wherein said probe comprises SEQ ID NO: 3 and at least one fluorochrome selected from fluorescein isothiocyanate (FITC), Texas Red, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM), and N,N,N',N'-tetramethyl-6-carboxyrhodamine (TAMRA).

4. A nucleic acid probe for detecting an amplification product produced by the isolated primer pair of claim 2, wherein said probe comprises SEQ ID NO: 3 and at least one fluorochrome selected from fluorescein isothiocyanate (FITC), Texas Red, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM), and N,N,N',N'-tetramethyl-6-carboxyrhodamine (TAMRA).

* * * * *